United States Patent [19]

Johnson et al.

[11] 4,447,646

[45] May 8, 1984

[54] PROCESS FOR THE PURIFICATION OF TEREPHTHALIC ACID

[75] Inventors: Griffin I. Johnson; Judy E. Kiefer, both of Kingsport, Tenn.

[73] Assignee: Eastman Kodak Company, Rochester, N.Y.

[21] Appl. No.: 461,705

[22] Filed: Jan. 28, 1983

[51] Int. Cl.$^3$ .............................................. C07C 51/42
[52] U.S. Cl. ................................... 562/487; 562/416; 562/417; 562/485
[58] Field of Search ................ 562/416, 417, 485, 487

[56] References Cited

U.S. PATENT DOCUMENTS

| | | | |
|---|---|---|---|
| 3,431,296 | 3/1969 | Ichikawa et al. | 562/487 |
| 3,887,613 | 6/1975 | Blay | 562/487 X |
| 4,201,871 | 5/1980 | Tanouchi et al. | 562/486 |
| 4,211,882 | 7/1980 | Komatsu et al. | 562/416 |
| 4,314,073 | 2/1982 | Crooks | 562/416 |

*Primary Examiner*—Natalie Trousof
*Assistant Examiner*—Vera C. Clarke
*Attorney, Agent, or Firm*—David E. Cotey; Daniel B. Reece, III

[57] ABSTRACT

The present invention provides an improved process for the purification of crude terephthalic acid which has been produced by the oxidation of para-xylene. The process comprises contacting the crude terephthalic acid with oxygen-containing gas at a temperature of about 190° to 230° C. and a pressure of about 1,850 to 3,600 kPa in the presence of a solvent comprising an alkanoic acid which is preferably acetic acid. The process further comprises the use of a novel and surprisingly effective catalyst system. The catalyst system comprises cobalt, a bromide compound, and samarium, with the samarium being employed at a concentration of about 0.005 to 500 ppm.

17 Claims, No Drawings

PROCESS FOR THE PURIFICATION OF TEREPHTHALIC ACID

DESCRIPTION

Background of the Invention

The present invention relates to an improved process for the purification of crude terephthalic acid. More particularly, the invention relates to a novel process for recovering terephthalic acid of improved purity from a suspension containing crude terephthalic acid. The crude terephthalic acid is obtained by the liquid phase oxidation of para-substituted aromatic compounds in the presence of oxidizing catalyst.

In a typical known process for producing terephthalic acid, a para-dialkylbenzene is oxidized in acetic acid solvent with molecular oxygen in the presence of a catalyst. The para-dialkylbenzene generally used is para-xylene, and the catalyst generally used is a cobalt compound and a manganese compound. An oxidation promoter such as a bromine compound, methyl ethyl ketone, paraldehyde, or acetaldehyde is occasionally used. When para-xylene is oxidized in the liquid phase in acetic acid and in the presence of a catalyst, the product terephthalic acid, being very difficultly soluble in acetic acid, crystallizes out of the solvent acetic acid, forming a suspension. The suspending medium, that is, the acetic acid, contains a small amount of terephthalic acid dissolved therein, catalyst, unreacted para-xylene, intermediate oxidation products such as para-tolualdehyde, para-toluic acid, 4-carboxybenzaldehyde, and other organic impurities which may cause discoloration.

In order to reduce the concentration of such color-causing impurities, the crude terephthalic acid is generally subjected to a further purification treatment. One such treatment which has been known in the art involves heating the crude terephthalic acid with acetic acid, propionic acid, or butyric acid until it is dissolved, and then cooling the solution to crystallize the terephthalic acid.

Another purification process is disclosed in U.S. Pat. No. 3,431,296. This process involves contacting a suspension composed of 6 to 100 parts by weight of crude terephthalic acid in 100 parts by weight of an aliphatic monocarboxylic acid of 2 to 4 carbon atoms (or a defined aqueous solution thereof) with molecular oxygen-containing gas at 180° to 230° C. in the presence of a cobalt compound. This patent does not contemplate the use of any additional catalyst components.

Other disclosures, e.g., U.S. Pat. No. 4,314,073, U.S. Pat. No. 4,201,871, and Japanese Kokai No. 135,939/74 teach purification processes involving secondary or continuing oxidations (such as that discussed immediately above) wherein the mother liquor from the primary oxidation stage is displaced or diluted by fresh acetic acid. Such secondary and/or continuing oxidations typically utilize catalyst systems comprising cobalt, manganese, and/or bromide components.

U.S. Pat. No. 4,211,882 discloses a process for producing terephthalic acid by oxidizing p-tolualdehyde. The oxidation is conducted in the presence of a catalyst consisting of a manganese compound, a cobalt compound, a bromine compound, and at least one compound selected from the group consisting of chromium compounds, iron compounds, nickel compounds, and lanthanide metal compounds. Chromium compounds, lanthanum compounds, and cerium compounds are preferred examples of the fourth catalyst component. It is further disclosed in U.S. Pat. No. 4,211,882 that the invention was proposed as a solution to the problem of blackening of terephthalic acid produced by the oxidation of p-tolualdehyde as raw material. The blackening was stated to be due to the presence of manganese in the product terephthalic acid. Therefore, the source of the discoloration of the crude terephthalic acid is different from that involved in the production of terephthalic acid by the oxidation of p-xylene, as in the present application.

It has now been found that the purification of crude terephthalic acid produced by the oxidation of para-xylene can be dramatically improved by employing a secondary oxidation stage which utilizes a catalyst system comprising cobalt, a bromide compound, and samarium.

SUMMARY OF THE INVENTION

The present invention provides an improved process for the purfication of crude terephthalic acid which is produced by the oxidation of para-xylene. The purification process comprises contacting the crude terephthalic acid with oxygen-containing gas at elevated temperature and pressure in the presence of a solvent comprising at least one lower alkanoic acid and a catalyst system comprising cobalt, a bromide compound, and samarium. The samarium is employed in the catalyst system at a concentration of about 0.005 to 500 ppm.

DETAILED DESCRIPTION OF THE INVENTION

The present invention provides an improved process for the purification of crude terephthalic acid. The crude terephthalic acid which is utilized in the process of the present invention is obtained by the oxidation of para-xylene. The oxidation of para-xylene to crude terephthalic acid is well known in the art, and any known procedures for accomplishing the primary oxidation can be employed. However, the process of the present invention is most advantageously practiced in conjunction with a primary oxidation which employs a lower alkanoic acid (i.e., alkanoic acid having 2 to 4 carbon atoms; e.g., acetic acid) and which employs a catalyst system comprising cobalt and a bromide compound. Other known processes involve the use of additional catalyst components, such as manganese.

The purification process of the present invention involves the secondary oxidation of the crude terephthalic acid produced in a primary oxidation, such as that described above.

The purification process comprises contacting the crude terephthalic acid with oxygen-containing gas. Preferred oxygen-containing gases include air and other mixtures of nitrogen and oxygen. One such convenient mixture which can be used in the process of the present invention is the vent gas from the primary oxidation which ordinarily comprises about 5 to 20% oxygen. It has been found that such a mixture containing less oxygen than does air gives rise to reduced acid losses during the course of the purification process.

The crude terephthalic acid is contacted with the oxygen-containing gas at elevated temperature and pressure. The purification process is preferably conducted at relatively low temperatures of about 190° to 230° C. The purification is preferably conducted at a pressure of 1850 to 3600 kPa (about 250 to 500 psig).

The purification process of the present invention is conducted in the presence of a solvent comprising at least one lower alkanoic acid. By "lower alkanoic acid" is meant alkanoic acids having 2 to 4 carbon atoms. Especially preferred as a lower alkanoic acid is acetic acid. In especially preferred embodiments, the solvent comprises a mixture of water and acetic acid which has a water content of about 5% by weight. The solvent is conveniently and preferably obtained by displacing about 80 to 90% of the mother liquor from the primary oxidation with fresh, wet acetic acid containing about 5% water. The exchange may be accomplished in any convenient apparatus but can perhaps most easily be accomplished in a centrifuging apparatus such as one or more cyclones.

The purification process of the present invention is conducted in the presence of a catalyst system which comprises cobalt, a bromide compound, and samarium. Additional catalyst components are not necessary to the practice of the present invention.

The residual mother liquor from the primary oxidation supplies the necessary cobalt and bromide catalyst components for the purification procedure when the solvent for the purification procedure is obtained by partial displacement of the primary oxidation mother liquor. If the solvent for the purification process consists totally of fresh acetic acid (or a mixture thereof with water), then additional cobalt and bromide values must be added to the system. When sufficient cobalt and bromide values are not provided together with the residual mother liquor, these values may be provided in elemental, combined, or ionic form. For example, cobalt may be provided as cobalt metal, as inorganic cobalt salts, such as halides, nitrates, and oxides of cobalt, or as organic cobalt compounds, such as cobalt acetate, cobalt naphthenate, etc. The bromide component may be added as elemental bromine, hydrogen bromide, sodium bromide, ammonium bromide, potassium bromate, tetrabromoethane, benzyl bromide, etc.

The cobalt component of the catalyst system of the present process can be present in a concentration of about 200 to 500 ppm, based on the concentration of cobalt in the entire reaction system. Preferably, the concentration of cobalt is about 300 to 400 ppm.

The bromide catalyst component is present in the purification process in a concentration of about 100 to 400 ppm, based on the total concentration of bromide (covalent and ionic) in the entire reaction system. In preferred embodiments, the bromide component is present in a concentration of about 250 to 400 ppm.

The catalyst system of the purification process of the present invention further comprises samarium. It has been observed that the inclusion of samarium in the catalyst system of the present purification process dramatically improves the effectiveness of the process, as will be further illustrated by the examples below. The samarium which is employed in the catalyst system may, like the other catalyst components, be provided in elemental, combined, or ionic form. For example, the samarium may be added as the metal, as an inorganic salt, such as samarium nitrate, samarium chloride, or samarium oxide, or as an organic salt, such as samarium acetate. Samarium is also conveniently available commercially as one component of a commercial mixture of lanthanides. Such a mixture of lanthanides may be employed in the process of the present invention, provided that an effective concentration of samarium is provided in the reaction system.

The samarium component of the catalyst system is preferably added directly to the purification process of the present invention (i.e., the secondary oxidation). The samarium component may be added at the primary oxidation stage; however, the advantages, if any, of providing samarium at that stage have not been fully delineated.

The use of samarium in the catalyst system of the present invention is characterized by excellent catalytic activity at extremely low concentrations. The samarium catalyst component is preferably present in a concentration of about 0.005 to 500 ppm, based on the concentration of samarium in the total reaction system. Concentrations of about 0.01 to 500 ppm are preferred, with concentrations of about 0.1 to 500 ppm being especially preferred. While it is conceivable to employ concentrations of samarium above about 500 ppm, no significant advantages are to be expected from the use of such elevated concentrations. In fact, it has been observed that samarium concentrations as low as about 0.01 ppm demonstrate approximately the same effectiveness as higher concentrations around 500 ppm.

The invention will be further illustrated by the following examples although it will be understood that these examples are included merely for purposes of illustration and are not intended to limit the scope of the invention.

EXAMPLES 1-10

Examples 1-10 were conducted in a batch process mode and were performed in a rocking titanium autoclave. The crude terephthalic acid, containing about 5,000 to 8,000 ppm 4-carboxybenzaldehyde (4-CBA), was prepared by air oxidation of p-xylene utilizing a cobalt/bromide catalyst. The crude TPA and residual catalyst were slurried in a 95:5 acetic acid:water mixture. The resulting slurry was charged to the autoclave which was pressurized to about 36,000 kPa with air and was heated to 190° to 230° C. After one hour, the autoclave was cooled and vented. The product was separated from the mixture by filtration, washed with acetic acid, and dried under 20 inches Hg vacuum at 100° C. The results are given in Table I.

TABLE I

| Ex. No. | Temp. °C. | Co ppm | Br ppm | Sm ppm | 4-CBA in product ppm |
|---|---|---|---|---|---|
| 1 | 200 | 500 | 200 | 500 | 200 |
| 2 | 200 | 500 | 200 | 0.1 | 180 |
| 3 | 200 | 500 | 200 | 0 | 360 |
| 4 | 200 | 250 | 100 | 0.1 | 240 |
| 5 | 200 | 250 | 100 | 0 | 630 |
| 6 | 190 | 500 | 200 | 0.1 | 200 |
| 7 | 190 | 500 | 200 | 0 | 440 |
| 8 | 220 | 500 | 200 | 0.1 | 100 |
| 9 | 220 | 500 | 200 | 0 | 300 |
| 10 | 230 | 500 | 220 | 0.1 | 40 |

Examples 1-3 indicate that under constant conditions of temperature, cobalt concentration, and bromide concentration, the 4-CBA concentration attained using samarium is approximately half of that attained without using samarium. 4-CBA is generally considered to be the most seriously problematic impurity in the product terephthalic acid. Examples 1-3 further indicate that this excellent effectiveness of samarium is demonstrated both at 0.1 and 500 ppm of samarium.

Examples 4 and 5 indicate that the high activity of the catalyst system is maintained at reduced cobalt and bromide concentrations. Again, the 4-CBA concentration obtained when samarium is present in the catalyst system is much less (i.e., a reduction by about 62%) than that obtained in the absence of samarium.

Examples 6-10 further demonstrate the effectiveness of samarium in the purification process catalyst system. Examples 6-10 also indicate that improvements in purity are obtained with increases in temperature.

EXAMPLES 11-14

Examples 11-14 were conducted in a continuous process mode. The equipment used in these Examples included a 1.1 gallon stirred flow reactor and two six-gallon stirred product tanks, all constructed of titanium. Crude terephthalic acid, acetic acid, water, and catalyst were mixed in a 50-gallon stirred feed tank and were fed to the reactor with a positive displacement pump. The source of cobalt and bromide catalyst components was filtrate obtained from a CO/Br-catalyzed para-xylene oxidizer. Any additional bromide ion required was obtained from reagent grade HBr. The reaction system contained about 300 to 400 ppm cobalt, about 225 to 360 ppm bromide, and the indicated amounts of samarium. The crude terephthalic acid contained about 5,200 ppm 4-CBA and was obtained from the same para-xylene oxidizer as the Co and Br catalyst components. The gas which was fed to the reactor comprised about 5% oxygen in nitrogen. The reaction mixture comprised about 19% terephthalic acid in a 95:5 acetic acid:water mixture. The reactor provided an average residence time of about 1.4 to 2.0 hours. The process was conducted at a pressure of about 1,850 kPa and a temperature of about 190 to 195° C. The results of these Examples are given in Table II.

TABLE II

| Ex. No. | Temp °C. | Residence Time, Hrs. | Co ppm | Br ppm | Sm ppm | 4-CBA ppm |
|---|---|---|---|---|---|---|
| 11 | 195 | 1.4 | 300 | 360 | 0.0 | 1100 |
| 12 | 195 | 1.4 | 300 | 230 | 1.0 | 390 |
| 13 | 190 | 2.0 | 400 | 250 | 0.0 | 1300 |
| 14 | 190 | 2.0 | 400 | 225 | 1.0 | 340 |

It can be seen from a review of the data of Table II that, under approximately equivalent conditions, the presence of samarium in the catalyst system gave rise to a reduction of 4-CBA in the product terephthalic acid by a factor of about 3.

EXAMPLES 15-23

These examples were conducted in a batch process mode. The reactions were conducted in a rocking titanium autoclave. The crude terephthalic acid, which contained about 5,000 to 8,000 ppm 4-CBA, was prepared by air oxidation of para-xylene using a cobalt/bromide catalyst. The crude terephthalic acid, together with 500 ppm Co (added as the acetate) and 200 ppm bromide (added as aqueous HBr), was slurried in 95:5 acetic acid:water. The reaction mixture further included samarium, which was added as the acetate, in the indicated concentrations. The resulting slurry was charged to the autoclave, which was then pressurized to about 3,600 kPa with air and was heated to 200° C. After one hour, the autoclave was cooled and vented. The product was separated by filtration, washed with acetic acid, and dried. The results are given in Table III.

TABLE III

| Ex. No. | Sm, ppm | Initial 4-CBA in TPA (ppm) | Final 4-CBA in TPA (ppm) |
|---|---|---|---|
| 15 | 500 | 8000 | 200 |
| 16 | 200 | 8000 | 200 |
| 17 | 100 | 8000 | 225 |
| 18 | 50 | 8000 | 225 |
| 19 | 10 | 8000 | 250 |
| 20 | 0.1 | 5000 | 210 |
| 21 | 0.1 | 8000 | 180 |
| 22 | 0.01 | 5000 | 270 |
| 23 | 0 | 5000 | ~400 |

These Examples indicate the surprising effectiveness of samarium in the catalyst system of the present invention at concentrations ranging from 0.01 to 500 ppm.

The invention has been described in detail with particular reference to preferred embodiments thereof, but it will be understood that variations and modifications can be effected within the spirit and scope of the invention.

We claim:

1. In a process for the purification of crude terephthalic acid produced by oxidation of para-xylene, said purification process comprising contacting said crude terephthalic acid with oxygen-containing gas at elevated temperature and pressure in the presence of a solvent comprising at least one lower alkanoic acid and a catalyst system comprising cobalt and a bromide compound, the improvement comprising employing samarium in said catalyst system in a concentration of about 0.005 to 500 ppm.

2. The process of claim 1 wherein said purification is conducted at a temperature of about 190° to 230° C.

3. The process of claim 1 wherein said purification is conducted at a pressure of about 1,850 to 3,600 kPa.

4. The process of claim 1 wherein said purification is conducted in the presence of about 200 to 500 ppm cobalt.

5. The process of claim 1 wherein said purification is conducted in the presence of about 100 to 400 ppm bromide.

6. The process of claim 1 wherein said catalyst system comprises about 0.01 to 500 ppm samarium.

7. The process of claim 1 wherein said oxygen-containing gas comprises a mixture of nitrogen and oxygen.

8. The process of claim 7 wherein said oxygen-containing gas comprises about 5 to 20% oxygen.

9. The process of claim 1 wherein said solvent comprises at least one alkanoic acid having 2 to 4 carbon atoms.

10. The process of claim 1 wherein said solvent comprises acetic acid.

11. In a process for the purification of crude terephthalic acid produced by oxidation of para-xylene, said purification process comprising contacting said crude terephthalic acid with oxygen-containing gas at a temperature of about 190° to 230° C. and a pressure of about 1,850 to 3,600 kPa in the presence of a solvent comprising acetic acid and a catalyst system comprising about 200 to 500 ppm cobalt and about 100 to 400 ppm bromide, the improvement comprising employing samarium in said catalyst system in a concentration of about 0.01 to 500 ppm.

12. The process of claim 11 wherein said oxygen-containing gas comprises a mixture of nitrogen and oxygen, the oxygen comprising about 5 to 20% of said mixture.

13. The process of claim 11 wherein said solvent comprises a mixture of water and acetic acid having a water content of about 5%.

14. The process of claim 11 wherein said catalyst system comprises about 300 to 400 ppm cobalt.

15. The process of claim 11 wherein said catalyst system comprises about 250 to 400 ppm bromide.

16. The process of claim 11 wherein said catalyst system comprises about 0.1 to 500 ppm samarium.

17. A process for the purification of crude terephthalic acid produced by oxidation of para-xylene, said purification process comprising contacting said crude terephthalic acid with a mixture of nitrogen and oxygen comprising about 5 to 20% oxygen at a temperature of about 190° to 230° C. and a pressure of about 1,850 to 3,600 kPa in the presence of (i) a solvent comprising a mixture of water and acetic acid having a water content of about 5% and (ii) a catalyst system comprising about 300 to 400 ppm cobalt, about 250 to 400 ppm bromide, and about 0.01 to 500 ppm samarium.

* * * * *